United States Patent [19]

Santus et al.

[11] Patent Number: 5,527,545
[45] Date of Patent: * Jun. 18, 1996

[54] LIQUID-SUSPENSION CONTROLLED-RELEASE PHARMACEUTICAL COMPOSITION

[75] Inventors: Giancarlo Santus, Milan; Giuseppe Bottoni, Bergamo; Ettore Bilato, Padova, all of Italy

[73] Assignee: Recordati S.A. Chemical and Pharmaceutical Company, Chiasso, Switzerland

[*] Notice: The term of this patent shall not extend beyond the expiration date of Pat. No. 5,296,236.

[21] Appl. No.: 165,307

[22] Filed: Dec. 10, 1993

Related U.S. Application Data

[63] Continuation-in-part of Ser. No. 928,616, Aug. 10, 1992, Pat. No. 5,296,236, which is a continuation of Ser. No. 711,588, Jun. 6, 1991, abandoned, which is a continuation of Ser. No. 408,755, Sep. 18, 1989, abandoned.

[30] Foreign Application Priority Data

Dec. 11, 1992 [IT] Italy .................. MI92A2826

[51] Int. Cl.⁶ ........................... A61K 9/16
[52] U.S. Cl. ........... 424/490; 424/493; 424/494; 424/495; 424/498
[58] Field of Search ............... 424/490, 494, 424/495, 498

[56] References Cited

U.S. PATENT DOCUMENTS

| | | | |
|---|---|---|---|
| 3,904,682 | 9/1975 | Fried et al. | 260/520 |
| 4,009,197 | 2/1977 | Fried et al. | 260/473 |
| 4,803,079 | 2/1989 | Hsiao et al. | 424/468 |

FOREIGN PATENT DOCUMENTS

| | | |
|---|---|---|
| 903540 | 2/1986 | Belgium . |
| 308739 | 9/1988 | European Pat. Off. ...... A61K 31/205 |
| 313328 | 10/1988 | European Pat. Off. ......... A61K 9/46 |
| WO89/08448 | 9/1989 | European Pat. Off. ......... A61K 9/52 |
| 413533 | 8/1990 | European Pat. Off. ......... A61K 9/50 |
| 250374B1 | 5/1991 | European Pat. Off. ......... A51K 9/52 |
| 438249A1 | 7/1991 | European Pat. Off. ....... A61K 31/19 |
| 359195B1 | 12/1993 | European Pat. Off. ......... A61K 9/54 |
| WO85/04099 | 3/1985 | WIPO .............................. A61K 9/22 |

OTHER PUBLICATIONS

Cramer, J. A. et al., *JAMA* 261:3273–7. 1989.
Day, R. O. et al., *Clin. Pharm. Ther.* 31(6): 733–40, 1982.
Gibaldi, M. et al., *Pharmacokinetics* (Marcel Dekker, New York) pp. 451–7, 1982.
*United States Pharmacopeia* Edition XXII, NF XVII, pp. 1578–83, 1990.

*Primary Examiner*—D. Gabrielle Phelan
*Attorney, Agent, or Firm*—Darby & Darby

[57] ABSTRACT

Disclosed is a liquid-suspension controlled-release enteric-coated pharmaceutical formulation for the administration of naproxen, comprising (a) microgranules of naproxen and an excipient; (b) four successive coats of polymeric hydrophilic and hydrophobic materials, at least the innermost of said coats imparting controlled-release properties to said naproxen according to a predetermined release profile, and at least the outermost of said coats imparting resistance to dissolution in gastric fluids; and (c) a liquid administration vehicle. This composition enables the oral administration of naproxen as a single daily dose the adjustment of the dosage to a patient's requirements, and avoids detrimental effects of prolonged contact of naproxen with the gastric mucosa thus aiding oral intake and minimizing the drug's typical side effects.

10 Claims, 1 Drawing Sheet

LIQUID-SUSPENSION CONTROLLED-RELEASE PHARMACEUTICAL COMPOSITION

This application is a continuation-in-part of U.S. patent application Ser. No. 928,616 filed Aug. 10, 1992 (now U.S. Pat. No. 5,296,236) which is a continuation of Ser. No. 711,588, filed Jun. 6, 1991, in turn is a continuation of Ser. No. 408,755 filed Sep. 18, 1989 (both now abandoned).

FIELD OF THE INVENTION

The invention involves controlled-release pharmaceutical formulations in liquid dosage forms for the administration of naproxen.

BACKGROUND OF THE INVENTION (S)-6-methoxy-$\alpha$-methyl-2-naphtaleneacetic acid (naproxen) is a long-known non-steroid anti-inflammatory drug, which also has analgesic and antipyretic activity (U.S. Pat. Nos. 3,904,682 and 4,009,197).

Because of the anti-inflammatory and analgesic activities of naproxen, it is indicated for treating various forms of arthritis, such as rheumatoid arthritis, osteoarthritis, ankylosing spondylitis, and gout arthropathy; as well as for treating forms of extraarticular rheumatism, such as lumbar sciatica, myalgia, neuralgia, radicular syndromes, periarthritis, myofibrositis and the like.

Therapy generally involves the use of daily doses ranging from 250 mg to 1,000 mg of active ingredient and the formulations currently available for administration include tablets, capsules, granules for extempore suspension (oral route), suppositories (rectal route), vials (intramuscular route), gels and emulsions (topical route). All these formulations are essentially designed to make the active ingredient readily available in the body in order to ensure a rapid onset of the therapeutic effect.

In particular, with respect to the oral administration route, the wish to extend the duration of the therapeutic effect led to the development of controlled drug release formulations to enable a single daily administration. It is in fact known that once-daily administration enables better patient compliance with recommended dosages during therapeutic treatment. For instance, patient compliance is reported to vary from 87% for drugs taken once a day to 39% for drugs taken four times a day (J. A. Cramer et al., *JAMA* It. ed. 1, 601 (1989)).

Examples of formulations suitable for once-daily administration are reported in U.S. Pat. No. 4,803,079, which describes the use of a matrix in which the active ingredient is dispersed and released by diffusion, as well as in European Patent Application EP 458,249 which describes the use of slow release pellets for the administration of a delayed release dose together with a ready release dose; and in European Patent EP 250,374, which describes solid dosing units suitable for the controlled release of drugs, including naproxen, with zero order kinetics.

The main drawback of all of these applications is the final large size and high weight of the solid dosage unit. This is particularly true of dosages with a high active ingredient content (as is the case with naproxen). Thus, for instance, by applying the teachings of patent U.S. Pat. No. 4,803,079, a tablet containing 1,000 mg of active ingredient would have an overall weight of about 1,300 mg, a diameter of about 15 mm, and a thickness of about 7 mm.

Obviously, administration of a dosage unit with these dimensions and weight to patients with difficulty swallowing presents a problem. This is not a minor problem considering that, for the above types of diseases, the patient population that uses naproxen is generally made up of elderly individuals.

Even when the formulation is broken down into micro-units (granules or pellets), the need to avoid overdosing (which in the case of naproxen may induce torpor, heartburn, dyspepsia, nausea or vomiting) requires that the micro-units be enveloped in a container (e.g. a gelatine capsule). The container will have dimensions similar to the ones above, and, therefore, will not avoid swallowing problems.

A further disadvantage of the oral administration of solid controlled-release dosage forms in the case of naproxen is that the active ingredient carried either in a tablet or in a capsule may cause local gastrointestinal contact intolerance which may occasionally cause bleeding in the gastrointestinal tract, peptic ulcer or colitis.

The concentration of naproxen reaching a gut mucosal cell depends both upon the drug's concentration in the lumen of the gut and the plasma concentration of the drug in mucosal capillaries.

It is generally believed that the mucus barrier in patients susceptible to gastrointestinal contact intolerance is somewhat deficient. Naproxen penetrates this barrier, inhibits the formation of the prostaglandins that sustain the mucus barrier and thereby allows hydrogen ions from the gastric lumen to penetrate and damage the mucosa.

This phenomenon leads to a need for a drug formulation that would avoid the problems of dispersion and topical contact with the gastric and upper duodenal mucosa. In principle, these problems can be avoided by using an "enteric" coating, i.e. one that is stable at low pH and dissolves at a higher pH (defined in Remington's Pharmaceutical Science, 18th Ed., pages 1669–1679).

One solution to the problems caused by solid controlled-release dosage forms is to use liquid-suspension controlled-release formulations. To be effective, they must be particularly homogeneous, suspendable and palatable as well in a form that guarantees the required release profile, and must therefore be made up of particles of sizes and characteristics that will allow the above requirements to be met.

Generally, the requirement for such small dimensions means keeping the excipient quantity ratio low in order to preserve the ability of the formulation to remain in suspension and to avoid a "sand-like" sensation upon ingestion. It is also particularly important to maintain a high concentration of active ingredient in the microgranules when treatment conditions require a high dosage, as is the case with naproxen.

For instance, in the formulations described in the international patent application WO 89/8448, the enteric-coated granules have diameters larger than 0.5 mm and, therefore, are totally unsuitable for suspension in liquid formulations.

Examples of formulations dimensionally suitable for liquid suspension for the administration of naproxen are described in the Belgian patent BE 903,540, which claims a powder controlled-release composition consisting of particles of sizes ranging from 0.1 to 125 μm that are said to be suitable for the liquid administration of several drugs, including naproxen.

Copending commonly assigned U.S. patent application Ser. No. 928,616 (corresponding to EP 359,195) also describes a therapeutic system for liquid controlled-releasepharmaceutical compositions that can be used to administer naproxen. This system consists of microgranules coated first with a pH-insensitive (inner most) coating that imparts controlled release properties to the microgranules, followed by various alternate coats of lipophilic and hydrophilic materials so that the total size of the microgranules ranges from 50 to 500 μm. The microgranules form stable suspensions in liquid administration vehicles.

However, by applying the teachings of the foregoing third party patents and applications, no liquid suspension naproxen-containing formulations have been developed that are capable of achieving therapeutically effective naproxen levels by a single daily administration. Furthermore, none of the liquid formulations described in the above patent applications is designed to get through the gastric fluid barrier. In addition, the foregoing copending U.S. patent application Ser. No. 928,616 does not specifically disclose a liquid controlled release formulation for naproxen suitable for a once-a-day administration nor a naproxen containing liquid formulation capable of withstanding gastric fluid.

It is thus an object of the present invention to provide a controlled-release pharmaceutical dosage form in liquid suspension delivering therapeutic levels of naproxen in the blood stream of a patent with a single daily administration, while avoiding the detrimental effects of prolonged contact of naproxen with the gastric mucous membrane.

SUMMARY OF THE INVENTION

It has now been found that a controlled-release pharmaceutical dosage form suitable for a once-daily administration of naproxen in a liquid suspension can be achieved using a multiplicity of microgranules containing naproxen as an active ingredient, which are coated with a series of successive coatings comprising:

a first coating applied directly to the microgranules that imparts controlled-release properties and contains polyethylene glycol as one ingredient;

a second coating applied to the first coating and having hydrophilic characteristics a third coating applied to the second coating and having lipophilic characteristics, and a fourth outermost coating having hydrophilic characteristics and containing cellulose acetate phthalate (CAP) or another polymer or polymers having the property of forming enteric coatings. The outermost coating imparts resistance to dissolution of naproxen in gastric fluids. Preferably, the total number of coatings is four.

The coated microgranules, which after coating have sizes ranging from about 50 to about 500 μm, are preferably combined with such optional ingredients as suspending, sweetening, buffering, preserving, or flavoring agents, or mixtures thereof. They can then be suspended in water or other physiologically acceptable mediums to obtain a liquid dosage form. Dosages can be adjusted by administering different amounts of the final liquid dosage form.

DETAILED DESCRIPTION OF THE INVENTION

Figure 1:
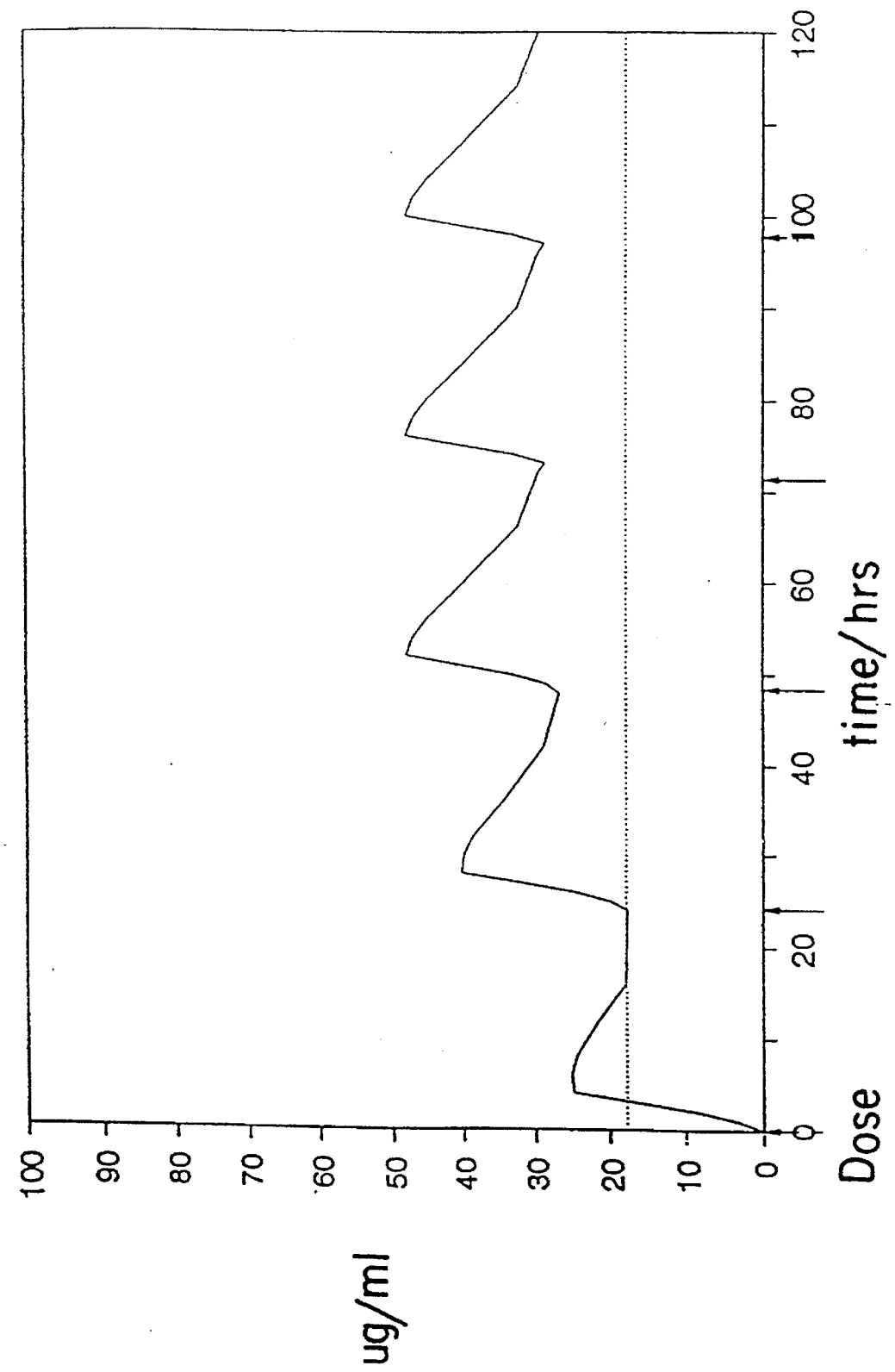
FIG. 1 is a graph showing simulated steady state blood levels of naproxen over five days after once a day administrations of naproxen.

The disclosure of U.S. patent application Ser. No. 928,616 is hereby incorporated by reference in its entirety.

The Composition of the present invention comprises a multiplicity of microgranules comprising a mixture of naproxen and excipients and having homogeneously smooth surfaces that permit uniform disposition of coatings (e.g., substantially spherical surfaces). The microgranules are preferably prepared as disclosed in copending U.S. patent application Ser. No. 928,616 and are then coated. The series of four coatings sequentially applied one on top of the other that may comprise for example (i) ethylcellulose plus plasticizer and polyethylene glycol; (ii) cellulose acetate phtalate and plasticizer; (iii) one or more waxes and (iv) cellulose acetate phtalate and plasticizer.

This formulation thus preserves the release characteristics of the dosage forms that are carried in it. It can be designed either as a liquid dosage formulation that remains stable for a relatively long period of time, or as a dry formulation that is reconstituted with water when needed and then remains stable throughout the period of treatment.

Since a significant improvement in patient compliance can be achieved by the present invention, its advantages in terms of reducing the number of daily doses while being convenient to administer and to swallow are clear. Additionally, an improved therapeutic response can be expected as the dosage can be adjusted to individual requirements simply by measuring the required suspension volumes. Finally, the outermost coating enhances local gastrointestinal contact tolerance, thus reducing undesirable side effects.

In detail, in a preferred embodiment, the present invention comprises a liquid measurable enteric-coated controlled-release pharmaceutical composition that includes:

1) Dosage forms for the controlled release of naproxen having sizes ranging after coating between 50 and 500 μm (preferably 90 and 300 μm), capable of remaining easily in suspension in a liquid for prolonged periods of time, each of said forms comprising:

a) a mixture of naproxen and excipients treated so as to form microgranular cores of small size, substantially uniform surface, lacking sharp or discontinuous morphology and permitting depositions of uniform coatings thereon to ensure reproducibility and uniform distribution of the successive coatings;

b) a first coating in contact with said microgranular cores imparting controlled release properties to the naproxen contained in the core, said coating containing polyethylene glycol;

c) a second hydrophilic coating on top of the first coating;

d) a third lipophilic coating on top of the second coating;

e) a final outer coating with "enteric" characteristics, meaning that it resists dissolution in gastric fluids but disintegrates in the small intestine. The last coating contains an enteric coating forming polymer (such as CAP) and if appropriate a plasticizer.

2) A vehicle system for the above controlled-release forms comprising either:

a) a dry mixture of suspending agents, sweetening agents and the controlled-release forms described in 1), a formulation that can be reconstituted into a liquid dosage form by suspension in an aqueous medium when needed; or b) an aqueous solution of the above suspending and sweetening agents in which the controlled release forms described in 1) can be suspended and maintained in optimum release conditions for extended periods of time.

In accordance with the present invention it has now been found that granules with a high content of active ingredient (more than 50% and preferably 80–90% by weight), uniform surfaces, preferably almost spherical shapes, apparent densities ranging between 300 and 800 g/l (preferably 500–600 g/l) and very low friabilities, can be obtained by wet-mixing naproxen and excipients by known techniques described in U.S. patent application Ser. No. 928,616 and EP 359,195.

The microgranulate is then evaluated for particle size distribution and density. This allows the calculation of the surface area of the microgranulate (as described below), which in turn allows the deposition of a reproducible and uniform amount of coating on the microgranules.

By mathematical processing of the particle size distribution data, the $d_g$ (mean geometric diameter) and $\sigma_g$ (standard deviation) of particle size distribution are calculated. Then $d_{vs}$ is calculated as follows from $d_g$ and $\sigma_g$: log $d_{vs}$=log $d_g$−1.151 log$^2$ $\sigma_g$, where $d_{vs}$ is the diameter volume-surface.

The surface area is then derived by means of the following formula: surface area=$6/P_g \cdot d_{vs}$ wherein $P_g$ is the apparent density.

By knowing the surface area, it is then possible to apply a constant amount of coating on the microgranules since a given coating amount (in g/m$^2$) is directly proportional to the surface area. After coating, the microgranules have a size within the range of 50–500 μm, preferably 90–300 μm. It should be noted, however, that coating does not substantially affect the size of the microgranules.

Examples of the elements that comprise the pharmaceutical formulation of the present invention are described below without limitation:

Microgranular Cores—1a)

The excipients used to make the cores can be chosen from those commonly used in wet mixing, such as dibasic calcium phosphate, lactose, microcrystalline cellulose, starch, talc, sugars, polyvinylpyrrolidone, polyvinylpyrrolidone/vinyl acetate copolymer and the like. The mixing liquid can be water or a solvent that can be mixed with water such as, for instance, ethyl alcohol or other commonly used alcohols, or a mixture of water and alcohol.

In accordance with the present invention, the granulate is then coated in successive stages with coatings of different compositions, using known coating techniques. Nonlimiting examples of each type of coating are given below:

Coating That Controls Release—1b)

A cellulose derivative capable of imparting release control characteristics, such as ethyl cellulose is mixed with a plasticizer such as diethyl phthalate (in an amount within the range of 10–30% by weight of the total mixture exclusive of solvents) in the presence of polyethylene glycol. The plasticizer may be omitted if water is used as the solvent.

The addition of 0.1–5% polyethylene glycol to the coating mixture imparts to the coating responsible for controlling release additional hydrophilic properties that enhance the diffusion of poorly water-soluble substances such as naproxen.

Hydrophilic Coating—1c)

Hydrophilic substances such as methyl cellulose, methacrylic acid copolymers, or polyvinylpyrrolidone may be used for this coating.

Lipophilic Coating—1d)

Fatty substances such as mono-, di- or triglycerides of fatty acids having 6 to 32 carbon atom chains, carnauba wax, beeswax, candelilla wax, fatty alcohols, and fatty acids may be used for this coating.

Enteric Coating—1e)

The same substances that make up this coating 1e) may also be used as ingredients for the second (hydrophilic) coating 1c). The outermost enteric coating contains cellulose acetate phthalate (or another polymer or polymers having the property of forming enteric coatings) and a plasticizer. See, Remington, supra, and USP XXII 724, p. 1380–81, 1990.

Plasticizers are preferably added to type 1c) as well as to type 1e) coating materials. The choice of a plasticizer for these coatings depends on whether it will be used for a wet process or for a process that uses organic solvents. (As stated above, plasticizer is not necessary when water is the only solvent.) Chlorinated solvents such as chloroform, alcohols such as ethanol, methanol or isopropyl alcohol, ketones such as acetone or methyl ethyl ketone, and different mixtures of the above solvents can be used as coating solvents instead of water. Mixtures of water and one or more water-miscible organic solvents can also be used.

Plasticizers that can be used include without limitation diethyl phthalate, dibutyl sebacate, triacetin, trialkylcitrate, vegetable oil, acetylated glycerides, polyethylene glycol or propylene glycol. Choice of plasticizer is within the skill in the art. The preferred plasticizer for use in the present invention is diethyl phthalate. The amount of plasticizer that is used varies with the coating substance and is within the skill in the art. Generally, the plasticizer comprises 10–30% (w/w) of the total polymeric mixture exclusive of solvents.

Vehicle—2a) and 2b)

The granulate coated according to the above procedures is then combined with a vehicle to form either a solid mixture that can be suspended extempore when needed or a suspension ready for use.

In addition to the coated microgranules comprising controlled-release dosage forms of the active ingredient, the ingredients which make up the vehicle are:

suspending and bodying agents such as cellulose esters, microcrystalline cellulose, alginic acid derivatives, and polyvinylpyrrolidone derivatives;

sugars such as sucrose and sorbitol;

buffering agents such as citric acid and sodium nitrate, glycine and hydrochloric acid, sodium and potassium phosphates;

preservatives and bacteriostatic agents such as p-hydroxybenzoic acid esters; and various flavorings and sweeteners commonly used in pharmaceuticals.

In addition to the above ingredients, the formulation includes water or mixtures of water and co-solvents such as a glycol, an alcohol, and glycerin.

The methods, tables and examples provided below are intended to more fully describe preferred embodiments of the invention and to demonstrate its advantages and applicability without limiting its scope.

EXAMPLE 1

Preparation of the Microgranulate

A mixture made up of 3,200 g naproxen, 400 g polyvinylpyrrolidone and 400 g lactose was mixed for 5 minutes so as to ensure good homogeneity. 500 ml of water atomized at a 2 bar pressure were then added to the mixture under stirring at a flow rate of 35 ml/min. The granulate was made spheroidal by stirring the mixture for an additional 10 minutes. The spheroidal product was then dried for about 2 hours on a temperature-controlled static bed at 35° C. until the residual humidity was reduced to a level of 4–5% by weight. The spheroidal product was sieved through 0.6 mm sieves until a granulate with a size range of 90 to 300 μm and a spheroidal shape with no particular surface roughness or unevenness was obtained.

EXAMPLE 2

500 ml of atomized water at a 15 ml/min flow rate and a 2 bar pressure were added to a mixture made up of 3,560 g naproxen and 440 g polyvinylpyrrolidone and mixed as described in Example 1. The granulate was then made spheroidal, dried and sieved as described above.

EXAMPLE 3

450 ml of atomized water at a 20 ml/min flow rate and a 2 bar pressure were added to a mixture made up of 3,200 g naproxen, 400 g polyvinylpyrrolidone and 400 g dibasic calcium phosphate dihydrate and mixed as described in Example 1. The granulate was then made spheroidal, dried and sieved as previously described.

EXAMPLE 4

500 ml of atomized water at a 15 ml/min flow rate and a 2 bar pressure were added to a mixture made up of 3,200 g naproxen, 400 g polyvinylpyrrolidone, 200 g lactose and 200 g dibasic calcium phosphate dihydrate mixed as described in Example 1. The granulate was then made spheroidal, dried and sieved as previously described.

In general, the preferred mean geometric diameters for the uncoated microgranules are within the range of 120–200 μm (most preferred: 130–170 μm) with a standard deviation of 1.4–2.0 (most preferred: 1.5–1.8). The preferred apparent density is 1.2–1.5 g/ml (most preferred 0.5–0.66 g/ml) and packed density is 0.5–0.9 g/ml (most preferred: 0.55–0.8 g/ml).

The formulations that can be used for the successive coatings are described in succeeding Examples, as follows: First coating (examples 5–7); second coating (examples 8–10); third Coating (examples 11–15); and fourth coating (Examples 16–18).

EXAMPLE 5

Coating of Microgranulate First Coating in Contact with Core 500 g of microgranulate prepared as in Example 1 were introduced into a fluid-bed coating apparatus, into which air heated to a temperature of 40°–45° C. was blown at a rate of 40–45 m³/hour, and turbulence stirred for 1 minute. The microgranulate was sprayed, at a 2 bar pressure and a 16 g/min flow rate, with a solution having the following percent composition by weight:

| | |
|---|---|
| Ethyl cellulose | 3.00 |
| Diethyl phthalate | 1.00 |
| Polyethylene glycol | 0.10 |
| Ethyl alcohol | 21.35 |
| Chloroform | 74.55 |

The quantity of material used to achieve a given coating thickness is dependent on the total surface area of the granulate to be coated. For example: 585 g of the above solution are sprayed to obtain 1.6 g/m² coating, whereas 731 g of the same are necessary to obtain 2.0 g/m² coating. Surface area can be determined as described above. The coating thickness is selected for the most favorable dissolution profile by routine experimentation. Once selected, the optimum coating thickness is kept constant.

EXAMPLE 6

Following an operating procedure identical to that described in Example 5, the microgranulate may be coated with a solution having the following percent composition by weight:

| | |
|---|---|
| Ethyl cellulose | 2.5 |
| Diethyl phthalate | 1.0 |
| Polyethylene glycol | 0.2 |
| Ethyl alcohol | 96.3 |

EXAMPLE 7

Following an operating-procedure identical to that described in Example 5, the microgranulate may be coated with a solution having the following percent composition by weight:

| | |
|---|---|
| Ethyl cellulose | 3.0 |
| Diethyl phthalate | 1.0 |
| Ethyl alcohol | 21.0 |
| Chloroform | 75.0 |

EXAMPLE 8

Second Coating (Hydrophilic Coating)

The same operating procedure described in Example 5 for applying the first coating was also used to apply the hydrophilic coating. A solution having the following percent composition was applied at a 2 bar pressure and an 8–10 g/min flow rate:

| | |
|---|---|
| Methacrylic acid copolymer (Eudragit E ®) | 12.5 |
| Acetone | 35.0 |
| Isopropyl alcohol | 52.5 |

The amount of solution used for the second coating depends upon the amount used for the first coating. For example, 155 g of the above solution are used when 1.6 g/m² of the first coating is applied, whereas 196 g of the same are necessary when 2.0 g/m² is used.

EXAMPLE 9

Alternatively, the solution used to apply the second coating may comprise the following percent composition by weight:

| | |
|---|---|
| Methylcellulose | 3.0 |
| Water | 97.0 |

EXAMPLE 10

Another solution suitable for the second coating layer has the following percent composition by weight:

| | |
|---|---|
| Polyvinylpyrrolidone | 5.0 |
| Water | 95.0 |

EXAMPLE 11

Third Coating (Lipophilic Coating)

A solution having the following percent composition by weight was applied to the second coating using the same pressure and flow conditions described in Example 5:

| | |
|---|---|
| Glyceryl monostearate | 4.50 |
| White beeswax | 0.40 |
| Cetyl alcohol | 0.05 |
| Stearyl alcohol | 0.05 |
| Chloroform | 89.60 |
| Methanol | 5.40 |

The amount of solution used for the third coating depends upon the amount used for the first coating. For example, 577 g of the above solution are used when 1.6 g/m² of the first coating is applied, whereas 697 g of the same are necessary when 2.0 g/m² is used.

EXAMPLE 12

Alternatively, the third coating may be achieved using a solution having the following percent composition by weight:

| | |
|---|---|
| Glyceryl monostearate | 6.5 |
| Chloroform | 93.5 |

EXAMPLE 13

An alternative solution suitable for the third coating layer has the following percent composition by weight:

| | |
|---|---|
| Beeswax | 6.0 |
| Isopropyl alcohol | 5.0 |
| Chloroform | 89.0 |

EXAMPLE 14

A further alternative solution suitable for the third coating layer has the following percent composition by weight:

| | |
|---|---|
| Kaomel$^R$ | 6.0 |
| Methyl alcohol | 29.0 |
| Chloroform | 65.0 |

Kaomel$^R$ is a mixture of hydrogenated vegetable oils of non-lauric origin.

EXAMPLE 15

An alternative solution suitable for the third coating layer has the following percent composition by weight:

| | |
|---|---|
| Carnauba wax | 5.0 |
| Chloroform | 95.0 |

EXAMPLE 16

Fourth Coating (Enteric Coating)

The same operating procedure described in Example 8 for applying the second coating was used for the final enteric coating. The fourth coating had the following percent composition by weight:

| | |
|---|---|
| Cellulose acetate phthalate | 4.0 |
| Diethyl phthalate | 1.0 |
| Acetone | 71.2 |
| Isopropyl alcohol | 23.8 |

The amount of solution used for the fourth coating depends on the amount used for the first coating. For example, 155 g of the above solution are used when 1.6 g/m² of the first coating is applied, whereas 196 g of the same are necessary when 2.0 g/m² is used.

EXAMPLE 17

Alternatively, the fourth coating may be achieved using a solution having the following percent composition by weight:

| | |
|---|---|
| Cellulose acetate trimellitate | 4.0 |
| Diethyl phthalate | 1.5 |
| Acetone | 70.0 |
| Isopropyl alcohol | 24.5 |

EXAMPLE 18

An alternative solution suitable for the final coating layer has the following percent composition by weight:

| | |
|---|---|
| Hydroxypropylmethylcellulose phthalate | 4.0 |
| Diethyl phthalate | 1.0 |
| Acetone | 75.0 |
| Isopropyl alcohol | 20.0 |

EXAMPLE 19

Preparation of Controlled-Release Liquid Suspension 5.50 g microcrystalline cellulose, 0.50 g sodium carboxymethyl cellulose, 0.50 g sodium citrate, 0.75 g citric acid monohydrate, 0.25 g methyl p-hydroxybenzoate, 0.06 g propyl p-hydroxybenzoate, 0.05 g sodium chloride, 0.02 g glycyrrhizinated ammonium and 65.77 g sugar were mixed in a mixer-granulator after sieving through a 0.4 mm average mesh. After dispersing 0.05 g surfactant (Span 20) and 0.20 g antifoam (dimethylpolysiloxane) in 5 ml of water, the resulting liquid was mixed with the powder mixture and granulated in the mixer-granulator. After drying to constant humidity, the resulting granulate was mixed with 1.30 g tragacanth and 0.05 g powdered citrus flavoring.

25.0 g of controlled-release naproxen microgranules, obtained as described in Examples 1, 5, 8, 11 and 16, were finally mixed with the vehicle granulate so as to obtain 100 g of formulation ready to be suspended in sufficient water to yield a naproxen content of 750 mg in 10 ml of final suspension.

EXAMPLE 20

In Vitro Testing of Release

Release of naproxen from the formulation of the present invention was tested using apparatus II (paddle) described in the United States Pharmacopoeia Ed. XXI operating at 50 revolutions/min in 900 ml of a phosphate buffer (pH=7.4) having the following composition:

| | |
|---|---|
| Dibasic sodium phosphate dihydrate | g 14.40 |
| Monobasic sodium phosphate dihydrate | g 2.96 |
| Demineralized water | q.s. to ml 1,000. |

The active ingredient concentration was determined by measuring absorption at 332 nm in an ultraviolet spectrophotometer. Measurements were made directly or after separation by high performance liquid chromatography.

The release of naproxen was compared in microgranules prepared as described in Examples 5 and 7. Table 1 shows the naproxen percentages released by microgranules that differ from each other only with respect to the presence of polyethylene glycol in the first coatings.

TABLE 1

| Time | % Naproxen Released | |
|---|---|---|
| (Hours) | Example 5 | Example 7 |
| 1 | 41 | 15 |
| 2 | 55 | 21 |
| 4 | 67 | 30 |
| 8 | 79 | 44 |
| 12 | 85 | 53 |
| 24 | >90 | 65 |

It is clear that, conditions being equal, the use of polyethylene glycol as one of the ingredients of the first coating ensures an optimum control over the release of naproxen over 24 hours.

EXAMPLE 21

Testing of Resistance to Gastric Fluids

Testing of resistance to gastric fluids was performed using the six vessel apparatus described in the United Stated Pharmacopoeia Ed. XXII page 1580. Tests were carried out at 37° C. and 60 revolutions/minute in 750 ml 0.1N hydrochloric acid. Samples were taken after the first and second treatment hours. Microgranules prepared as described in Example 1 and sequentially coated as described in Examples 5, 8, 11 and 16 were compared with microgranules coated with a first layer of ethylcellulose without a superimposed enteric coating. The individual measured percentages of dissolved naproxen are reported in Table 2.

TABLE 2

| | % Naproxen Release | | |
|---|---|---|---|
| | Full coated | | 1st coat only |
| Samples | 1st Hour | 2nd Hour | 1st Hour |
| 1 | 1.3 | 2.1 | 16.0 |
| 2 | 1.0 | 2.0 | 18.0 |
| 3 | 1.6 | 1.9 | 18.0 |
| 4 | 1.3 | 2.0 | 17.5 |
| 5 | 1.4 | 1.8 | 16.0 |
| 6 | 1.3 | 1.9 | 19.0 |

When fully coated microgranules are used, the fraction of naproxen dissolved in the medium did not exceed 10% of the dose introduced; thus, the fully coated microgranules fulfill the USP XXII enteric-coating specification (e.g. USP Method A or USP General). By contrast, the release profiles of microgranules lacking the enteric coating exceed the USP limits even after the first hour.

EXAMPLE 22

Testing of Dissolution Stability with Time

Tables 3 and 4 show the stability at ambient temperature of two formulations containing microgranules prepared as described in Example 1 and sequentially coated as described in Examples 5, 8, 11 and 16, that differ from each other only in the quantity of material used for coating in relation to the surface area to be coated:

Table 3=1.6 g/m$^2$, Table 4=2.0 g/m$^2$

The release of naproxen was measured as described in Example 20; measurements were taken at the time of formulation and after 30 days of storage at ambient temperature.

TABLE 3

| (1.6 g/m$^2$) | | |
|---|---|---|
| Time | % Naproxen Release | |
| (Hours) | Initial | 30 Days |
| 1 | 41 | 42 |
| 2 | 55 | 55 |
| 4 | 67 | 68 |
| 8 | 79 | 80 |
| 12 | 85 | 85 |
| 24 | >90 | >90 |

TABLE 4

| (2.0 g/m$^2$) | | |
|---|---|---|
| Time | % Naproxen Release | |
| (Hours) | Initial | 30 Days |
| 1 | 20 | 22 |
| 2 | 27 | 30 |
| 4 | 38 | 42 |
| 8 | 52 | 55 |
| 12 | 59 | 60 |
| 24 | >80 | >80 |

With both formulations, the product retained unchanged release characteristics even after one month. Furthermore, the larger quantity of coating applied (Table 4) considerably slowed the active ingredient release. For this reason, the formulation represented in Table 3 is preferred.

EXAMPLE 23

Testing of Suspension in Vehicle

The formulation of Example 19 was tested for its ability to remain in suspension. This was done by stirring the formulation for about 30 seconds, and then pouring it into a graduated cylinder and measuring the height of the clear liquid against total liquid height at fixed times. After one hour all particles remained in suspension. After 24 hours, the height of the clear liquid was still only 5% of the total. The present suspension formulation thus ensures consistency and homogeneity of any different doses taken.

EXAMPLE 24

Bioavailability and Therapeutic Efficacy of Formulation

To test the bioavailability and therapeutic efficacy of the invention, a kinetic study was carried out according to a cross-over design in two periods using single doses.

The study was conducted in 6 healthy volunteers who received a single dose (750 mg) of a liquid controlled-release naproxen formulation (A) prepared as described in Example 19 and having the following composition:

| Ingredient | Weight % | Actual Weight (mg) |
|---|---|---|
| Naproxen c.r. microgranules | 25.00 | 937.5 |
| Citric acid | 0.75 | 31.2 |
| Sodium citrate | 0.50 | 20.8 |
| Microcrystalline cellulose | 5.50 | 230.0 |
| Sodium carboxymethyl-cellulose | 0.50 | 20.8 |
| Tragacanth gum | 1.30 | 54.1 |
| Methyl p-hydroxybenzoate | 0.25 | 10.4 |
| Propyl p-hydroxybenzoate | 0.06 | 2.5 |
| Sorbitan monolaurate | 0.05 | 2.0 |
| Dimethylpolysiloxane | 0.20 | 8.0 |
| Powdered citrus flavoring | 0.05 | 2.0 |
| Glycyrrhizinated ammonium | 0.02 | 0.8 |
| Sodium chloride | 0.05 | 2.0 |
| Sugar | 65.77 | 2840.0 |

In the above composition, 937.5 mg of naproxen microgranules contain 750 mg of naproxen. The total weight of the above composition is 4.16 g.

For comparison, a formulation of immediate-release granular naproxen (B) having the following composition was used:

| Ingredient | mg |
|---|---|
| Naproxen | 750.0 |
| Mannitol | 750.0 |
| Polyvinylpyrrolidone | 75.0 |
| Methacrylic acid copolymer | 112.5 |
| Sodium saccharin | 52.5 |
| Lemon flavoring | 150.0 |
| Citric acid | 130.5 |
| Silica | 7.5 |
| Sucrose | 2,467.5 | total weight: 4.5 g |

Blood samples were taken at different times and the naproxen plasma concentration was determined by high performance liquid chromatography and ultraviolet spectrometry. Table 5 shows the main pharmacokinetic parameters resulting from the trial.

TABLE 5

PHARMACOKINETIC PARAMETERS
(mean values ± S.D.)

| | $C_{max}$ (μg · h/ml) | $T_{max}$ (h) | $AUC_{0-\infty}$ (μg/ml) |
|---|---|---|---|
| NAPROXEN (A) | 27.12 (±11.3) | 6.0 (±1.8) | 946.51 (±311.21) |
| NAPROXEN (B) | 76.82 (±18.53) | 2.3 (±0.8) | 1,168.58 (±285.63) |

S.D. = Standard deviation
$C_{max}$ = (Peak concentration): the highest plasma concentration the drug reaches after the administration;
$T_{max}$ = (Time concentration) the time necessary to reach the $C_{max}$ value;
$AUC_{0-\infty}$ = (Area under the curve) the total area of the time-concentration profile and represents a measure of the bioavailability.

The relative bioavailability (F) of two different forms (A and B) administered at the same dosage and using the same administration route is given by the following formula:

$$F=AUC(A)/AUC(B) \times 100.$$

These data show that formulation (A) reduced $C_{max}$ considerably and extended $T_{max}$, indicating a relative bioavailability (F) equal to 81% as compared with the reference product (B).

A literature value of 18 μg/ml, which is considered the minimum plasma level ensuring therapeutic efficacy [Clin. Pharm. Ther. 31, 6 (1982)], was used as a reference value to assess therapeutic efficacy. FIG. 1 is a graph showing simulated steady-state blood levels after multiple administrations for 5 days, calculated in accordance with the pharmacokinetic parameters found. As can be seen, the present invention is capable of maintaining therapeutic levels even with a once-daily administration avoiding the initial peak effect and, therefore, minimizing any occurrence of side effects associated with it.

All documents cited herein are incorporated by reference.
What is claimed is:
1. A controlled-release pharmaceutical dosage form comprising:
a multiplicity of microgranules containing naproxen as an active ingredient and at least one excipient, said microgranules having substantially no controlled-release properties prior to coating,
a series of successive polymeric coatings that coat said microgranules, comprising:
a first coating applied directly to the microgranules, at least said first coating imparting controlled-release properties to said microgranules, said coating comprising polyethylene glycol as one ingredient thereof;
a second coating with hydrophilic characteristics;
a third applied coating with lipophilic characteristics; and
an outermost coating with hydrophilic characteristics, at least said outermost coating imparting resistance of said microgranules to dissolution in gastric fluids;
said microgranules after coating having sizes ranging from 50 to 500 μm.
2. The dosage form of claim 1, wherein said microgranules, prior to coating, have a homogeneous and uniformly smooth surface, a substantially spherical shape, an apparent density of between 300 and 800 g/l, and a low friability.

3. The dosage form of claim 1 wherein said microgranules, prior to coating, contain more than 50% naproxen by weight.

4. The dosage form of claim 2, wherein said microgranules, after coating, have dimensions of between about 90 and about 300 μm.

5. The dosage form of claim 1, wherein:

the excipient is a member selected from the group consisting of polyvinylpyrrolidone, lactose and dibasic calcium phosphate;

the first release-control imparting coating comprises a mixture of a cellulose derivative, a plasticizer, and polyethylene glycol;

the second coating comprises a member selected from the group consisting of methyl cellulose, methacrylic acid copolymers, polyvinylpyrrolidone, and mixtures of at least two of the foregoing;

the third coating comprises a member selected from the group consisting of mono-, di-, and triglycerides of fatty acids, waxes, fatty alcohols and fatty acids; and the outermost coating comprises a plasticizer and a member selected from the group consisting of polymers forming enteric coatings.

6. The dosage form of claim 1, wherein the first coating applied to said microgranules comprises diethyl phthalate in a range from about 10% to about 30% by weight compared to the weight of the total ingredients of the first coating mixture exclusive of solvents and further comprises polyethylene glycol in a range from about 0.1% to about 5% by weight compared to the total weight of the first coating mixture, exclusive of solvents.

7. The controlled release pharmaceutical dosage form of claim 1, wherein the second coating of hydrophilic material applied to the first coating comprises diethyl phthalate in a range from about 10% to about 30% by weight as compared to the total weight of the second coating mixture, exclusive of solvents.

8. The controlled release pharmaceutical dosage form of claim 5, wherein the outermost coating comprises cellulose acetate phthalate as the enteric coating forming polymer and, as the plasticizer, diethyl phthalate said diethyl phthalate being in an amount within the range from about 10% to about 30% by weight as compared to the total weight of the second coating mixture, exclusive of solvents.

9. A controlled release pharmaceutical dosage form comprising a liquid dosage formulation for immediate use said formulation containing the dosage form of claim 1 suspended in water.

10. A controlled release pharmaceutical dosage form comprising a liquid dosage formulation containing the dosage form of claim 1 suspended in a physiologically acceptable aqueous medium.

* * * * *

UNITED STATES PATENT AND TRADEMARK OFFICE
CERTIFICATE OF CORRECTION

PATENT NO.  : 5,527,545
DATED       : June 18, 1996
INVENTOR(S) : Giancarlo Santus; Giuseppe Bottoni and Ettore Bilato It is certified that error appears in the above-indentified patent and that said Letters Patent is hereby corrected as shown below:

On the title page, at section "[30]", delete "M192A2826" and substitute therefor--MI92A002826--.

Signed and Sealed this

Twenty-ninth Day of October 1996

Attest:

BRUCE LEHMAN

Attesting Officer        Commissioner of Patents and Trademarks